(12) United States Patent
Wortley et al.

(10) Patent No.: US 8,435,249 B2
(45) Date of Patent: May 7, 2013

(54) FLEXIBLE CONNECTION CATHETER TUNNELER AND METHODS FOR USING THE SAME

(75) Inventors: Ron Wortley, Salt Lake City, UT (US); Eric King, West Jordan, UT (US)

(73) Assignee: Medron, Inc., Salt Lake City, UT (US)

( * ) Notice: Subject to any disclaimer, the term of this patent is extended or adjusted under 35 U.S.C. 154(b) by 1058 days.

(21) Appl. No.: 10/814,318

(22) Filed: Mar. 31, 2004

(65) Prior Publication Data

US 2004/0230204 A1    Nov. 18, 2004

Related U.S. Application Data

(60) Provisional application No. 60/459,746, filed on Apr. 1, 2003.

(51) Int. Cl.
*A61F 11/00*      (2006.01)

(52) U.S. Cl.
USPC ........................................................ 606/108

(58) Field of Classification Search .......... 623/1.11, 623/23.72; 606/108, 190, 129, 1, 223; 403/677, 403/377; 604/43, 104, 158, 523, 533–536, 604/537–539, 164.01–164.08, 96.01, 157; 600/184; 425/255
See application file for complete search history.

(56) References Cited

U.S. PATENT DOCUMENTS

| | | | | |
|---|---|---|---|---|
| 17,272 A | * | 5/1857 | Garvey | 112/224 |
| 899,381 A | * | 9/1908 | Bradley | 112/224 |
| 4,626,240 A | * | 12/1986 | Edelman et al. | 604/43 |
| 5,405,329 A | * | 4/1995 | Durand | 604/164.01 |
| 5,437,680 A | * | 8/1995 | Yoon | 606/139 |
| 5,964,796 A | * | 10/1999 | Imran | 607/122 |
| 6,165,167 A | * | 12/2000 | Delaloye | 604/528 |
| 6,258,026 B1 | * | 7/2001 | Ravenscroft et al. | 600/200 |
| 6,921,396 B1 | * | 7/2005 | Wilson et al. | 604/508 |
| 2002/0099326 A1 | * | 7/2002 | Wilson et al. | 604/43 |
| 2002/0099327 A1 | * | 7/2002 | Wilson et al. | 604/43 |
| 2002/0193826 A1 | * | 12/2002 | McGuckin et al. | 606/200 |
| 2003/0163082 A1 | * | 8/2003 | Mertens | 604/43 |
| 2004/0167463 A1 | * | 8/2004 | Zawacki et al. | 604/43 |

FOREIGN PATENT DOCUMENTS

WO    WO 02/76333    *   3/2001

* cited by examiner

*Primary Examiner* — Gary Jackson
*Assistant Examiner* — Lindsey Bachman
(74) *Attorney, Agent, or Firm* — Kenneth E. Horton; Kirton McConkie

(57) ABSTRACT

Tunneling systems and methods or making and using such systems for implanting biological devices, especially catheters, are described. The tunneling system of the invention contains flexible connection tunnelers that contain multiple connection features that are of dissimilar lengths. When used for a multiple lumen catheter, the connection features are easier to separate and are easier to connect with the lumens of the catheter that are in different positions relative to the tunneler. Thus, the tunneling system contains a non-destructive connection between the catheter tip and the tunneler, as well as allowing for greater control during placement of the catheter.

17 Claims, 4 Drawing Sheets

FLEXIBLE CONNECTION CATHETER TUNNELER AND METHODS FOR USING THE SAME

CROSS-REFERENCE TO RELATED APPLICATIONS

This application claims priority of U.S. Provisional Patent Application No. 60/459,746 (filed Apr. 1, 2003), the entire disclosure of which is incorporated herein by reference.

FIELD OF THE INVENTION

The invention generally relates to medical devices and methods for making and using such medical devices. More particularly, the invention relates to medical devices for subcutaneous catheter placement, commonly known as tunnelers, and methods for making and using such tunnelers to place catheters, specifically hemodialysis catheters or related vascular access catheters.

BACKGROUND OF THE INVENTION

Catheters and their use as medical devices are well known in the art. To minimize kinking and/or any infection to the patient, the catheter runs parallel under the skin for a short distance before it enters the vascular system or other desired system of the body. To place the catheter in this position, accomplish this result, the physician typically makes a first incision in the catheter entry point, i.e., the access point in the skin and in the vessel wall. A second incision is also made at the catheter exit point in the skin a short distance away from the first incision. The distal tip of the catheter is then attached to a tunneler. The tunneler is inserted into the second incision and pushed under the skin until it exits the first incision, thereby creating a "tunnel" between the two incisions. The tunneler is then used to pull the catheter through the "tunnel" underneath the skin. The catheter tip is then removed from the tunneler and the catheter is pushed back through the vascular access incision into the vessel incision, thereby allowing external access to the vascular system.

There are numerous types of tunnelers known in the art, including metallic tunnelers. See, for example, U.S. Pat. No. 6,565,594, the disclosure of which is incorporated herein by reference. Metallic tunnelers are typically designed to produce a reaction force—against the friction of pulling the catheter through the tunnel—by using a mechanical interference fit between the tunneler connection point and the internal geometry of the catheter tip. The requirements (i.e., geometry) of the interference fit are usually very stringent due to the required reaction force. Examples of the interference fit include non-compliant sharp barbs, ridges and threads. This stringent geometry can damage the catheter tip and could result in tip detachment, compounding an already serious procedure with patient safety and catheter functionality concerns.

To minimize the required reaction force and decrease such problems, a tunneler sheath is often used. The tunneler sheath typically contains a tapered tube that slides over the tunneler/catheter connection. Despite the use of tunneler sheath, damage to the catheter tip still remains a distinct possibility.

Current tunneler designs often contain a tapered metallic or plastic rod with a small diameter (e.g., 0.125 inches or less) that facilitates passage underneath the skin. This small diameter—when accompanied with blood or medical fluids—often makes it difficult for the physician to grip the tunneler, resulting in slippage and loss of control during the tunneler/catheter connection procedure.

The existing connections between catheter tips and tunnelers typically contain only a single connection feature that is used in the lumen of the tip of a single or multiple lumen catheter. For multiple lumen catheters, the tunnelers typically have connection features with lengths that are substantially the same for each lumen. When such tunnelers are used with multi-lumen catheters having staggered tip geometry, it can be difficult to separate the connection features to allow one connection feature to enter the more distal lumen and the other to enter the more proximal lumen.

SUMMARY OF THE INVENTION

The invention includes tunneling systems and methods or making and using such systems for implanting biological devices, especially catheters. The tunneling system of the invention contains flexible connection tunnelers that contain multiple connection features that are of dissimilar lengths. When used for a multiple lumen catheter, the connection features are easier to separate and are easier to connect with the lumens of the catheter that are in different positions relative to the tunneler. Thus, the tunneling system contains a non-destructive connection between the catheter tip and the tunneler, as well as allowing for greater control during placement of the catheter.

BRIEF DESCRIPTION OF THE DRAWINGS

The following description of the invention can be understood in light of FIGS. 1-8, in which:

FIGS. 1-8 illustrate specific aspects of the invention and are a part of the specification. Together with the following description, the Figures demonstrate and explain the principles of the invention. The Figures presented in conjunction with this description are views of only particular-rather than complete portions of the systems and methods of making and using the tunneling systems according to the invention. In the Figures, the physical dimensions may be exaggerated for clarity. The same reference numerals in different drawings represent the same element, and thus their descriptions will be omitted.

DETAILED DESCRIPTION OF THE INVENTION

The following description provides specific details in order to provide a thorough understanding of the invention. The skilled artisan, however, would understand that the invention can be practiced without employing these specific details. Indeed, the invention can be practiced by modifying the illustrated method and resulting product and can be used in conjunction with apparatus and techniques conventionally used in the industry. For example, the invention is described for a two-connection tunneler that can be used for a dual lumen catheter. The invention, however, could easily be adapted for a three or four (or even more) connection tunneler. As well, the invention is described primarily in the context of a multi lumen catheter with a particular medical application. However, the invention could be used for other medical applications like vascular grafts, penile implants, as well as with medical single lumen catheters or tubes used in any industry that require placement with minimal damage to the tube.

The invention includes a tunneling system for implanting biological devices (i.e., catheters) and methods or making and using such systems. The system contains a flexible tunneler tip containing multiple connection features of dissimilar lengths for connecting to a catheter. The tunneling system also contains a tunneler shaft for the tunneling function. The tunneling system also contains a sheath for covering where the tunneler shaft and the tunneler tip connect.

Figure 1:
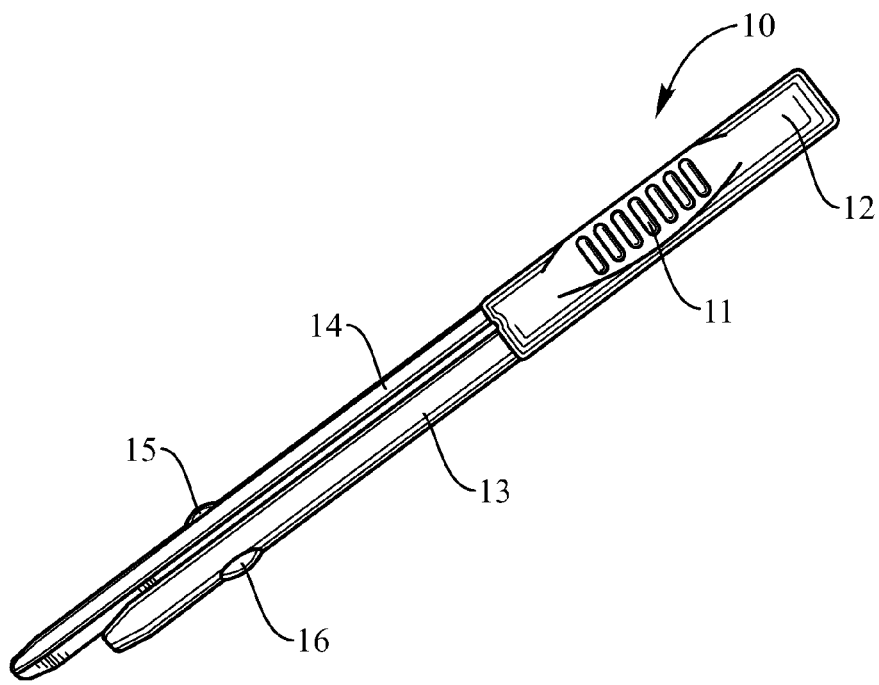
FIG. 1 is a side perspective view of a flexible connection catheter tunneler proximal tip in one aspect of the invention.
Figure 2:
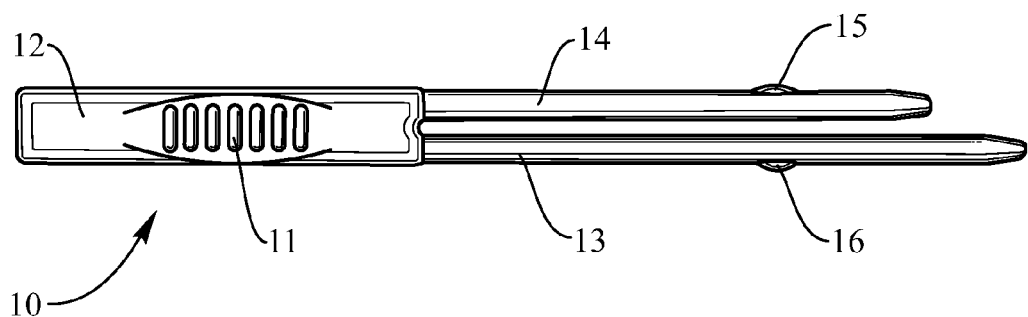
FIG. 2 is a left side view of the flexible connection catheter tunneler proximal tip of FIG. 1.
Figure 3:
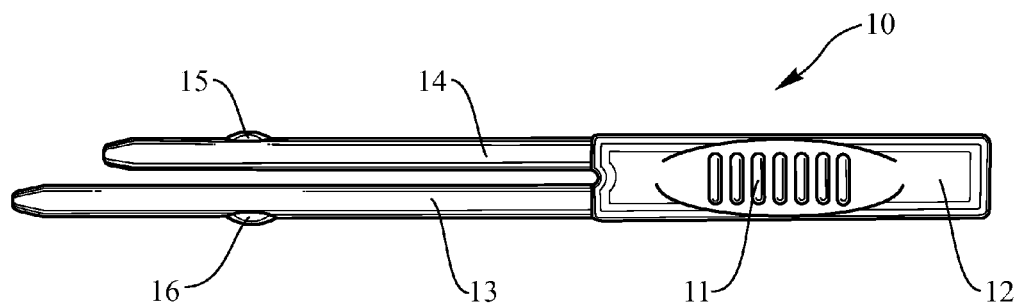
FIG. 3 is a right side view of the flexible connection catheter tunneler proximal tip of FIG. 1.

The tunneler tip is that part of the tunneling system that connects with the catheter. This connection occurs in a non-destructive connection that allows for a high degree of control during placement of the catheter. FIGS. 1, 2 and 3 depict one aspect of the tunneler tip of the tunneler system of the invention. In these Figures, the tunneler tip 10 (or tip 10) contains any suitable grasping or gripping means for the user, i.e., a physician. In one aspect of the invention, the gripping means includes grip member 12 with grip surface 11. Any additional or alternative grip member (and accompanying grip surface) for medical devices known in the art can be used in the invention.

The tip 10 also contains connector shafts (or shafts) for easy connection to the catheter (not shown) or other medical device. Any shafts known in the art can be used in the invention, including shafts 13 and 14 depicted in FIGS. 1-3. In one aspect of the invention, each of the shafts 13 and 14 can be tapered on their ends for easy insertion into and connection with the lumen of a catheter (or similar component of a medical device). The taper used on the shafts can be varied depending on the desired catheter with which the tunneler system will be used. In other words, the distal end has a smaller geometry that increases in size along the distance of the shaft until the final geometry size is obtained.

The connector shafts can be of the same length or of a different length. In one aspect of the invention, the shafts are a different length. The actual length of connector shafts 13 and 14 can be selected (and therefore varied) depending on the medical device in which it is used, i.e., the dual-lumen catheter. In one aspect of the invention, the difference in lengths between shaft 13 and shaft 14 also depend on the expected difference in the positions of the catheter lumens with which the tunneler of the invention will be used. In one aspect of the invention, the difference in lengths can range up to 20%, and typically ranges from about 5% to about 20%. Generally, the lengths of the connector shafts can vary up to about 6 cm. In one aspect of the invention, the lengths of the connector shafts can vary from about 1 to about 10 cm. Generally, the difference in lengths of the connector shafts can vary up to about 2 cm. In one aspect of the invention, the different lengths of the connector shafts can vary from about 1 to about 5 cm.

Each of the shafts 13 and 14 are flexible, thereby allowing easier connection of the tunneler with a catheter. The shafts can be made flexible using any known mechanism in the art. A first such mechanism is by using a flexible material such as flexible metals (i.e., Nitinol), or plastics. A second mechanism includes using corrugations in a portion—or all—of the shaft. A third mechanism includes using a plurality of slots, holes, grooves, discontinuities, series of links, or a combination thereof in a portion—or all—of the shaft.

The shafts also contain means for connecting the shaft to the catheter. Any such connection means known in the art can be used. In one aspect of the invention, and as depicted in FIGS. 1-3, the connection means comprises a protrusion 16 that is located on the outside of the shaft 13. A similar protrusion 15 is located on the outside of shaft 14. In certain aspects of the invention, a plurality of protrusions can be located on a single shaft. In one aspect of the invention, only one of the shafts is provided with a protrusion As well, the protrusions 15 and 16 could be replaced (or supplemented) with additional connection means that serve (or enhance) the same functions as the protrusions. For example, each connections shaft 13 and 14 could contain multiple protrusions of different sizes and shapes.

The protrusions are located in a position on the shaft what will facilitate connection with the lumen(s) of the catheter and as described below, connection with the sheath. Generally, the protrusions are located near the tip of the shaft, i.e., about 1 to about 2 cm away from the end of the shaft. The protrusions are configured with a size and shape that will facilitate connection with the catheter lumens and the sheath. In one aspect of the invention, the protrusions are circular or oval in shape with a diameter of about 5 mm and are raised above the surface of the shaft about 2 mm.

Figure 4:
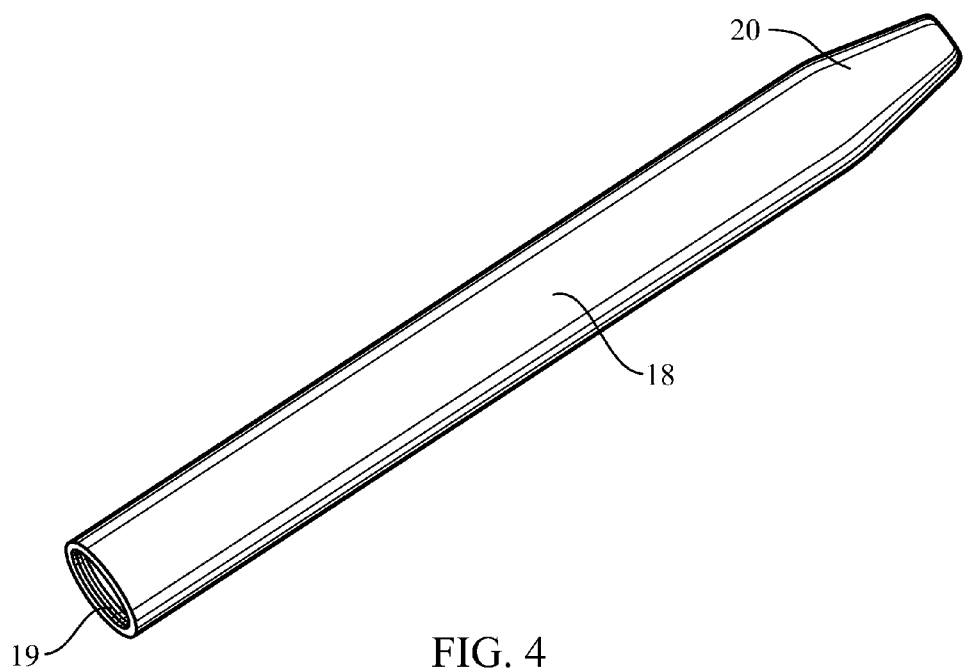
FIG. 4 is a side view of a tunneler sheath in one aspect of the invention.
Figure 5:
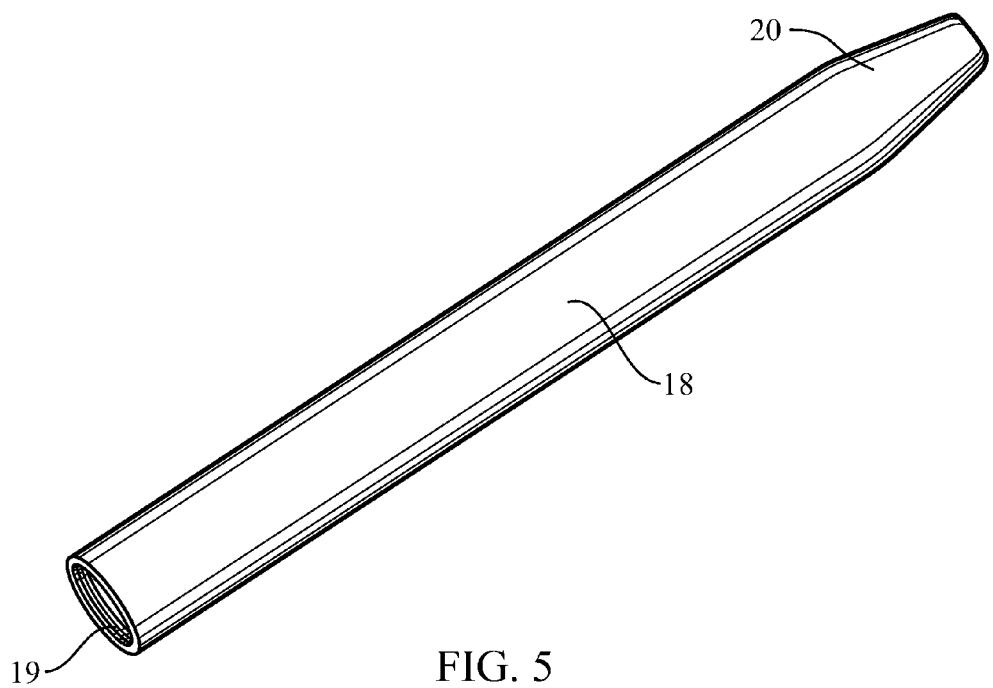
FIG. 5 is a sectional view of the tunneler sheath of FIG. 4.

Besides the tunneler tip, the tunneler system of the invention also contains a sheath. Any sheath that covers the tunneler tip (and the tunneler shaft described below), as well as distal end of the catheter tip, can be used in the invention. In one aspect of the invention, the sheath illustrated in FIGS. 4 and 5 is used in the tunneler system. As depicted in FIG. 4, the tunneler sheath 18 can contain a tapered tip 20. Since the sheath covers the tunneler shaft, the taper of the tip 20 should be configured to both easily cover the tunneler shaft 17. Any taper that functions in this manner can be used in the invention. In one aspect of the invention, the taper of the tip 20 is depicted in FIGS. 4 and 5 where the taper can range from about 5 to about 20 degrees. The sheath can be made from any material consistent with its function, including polypropylene, polyethylene, polycarbonate, and/or any other semi ridged polymer.

Figure 7:
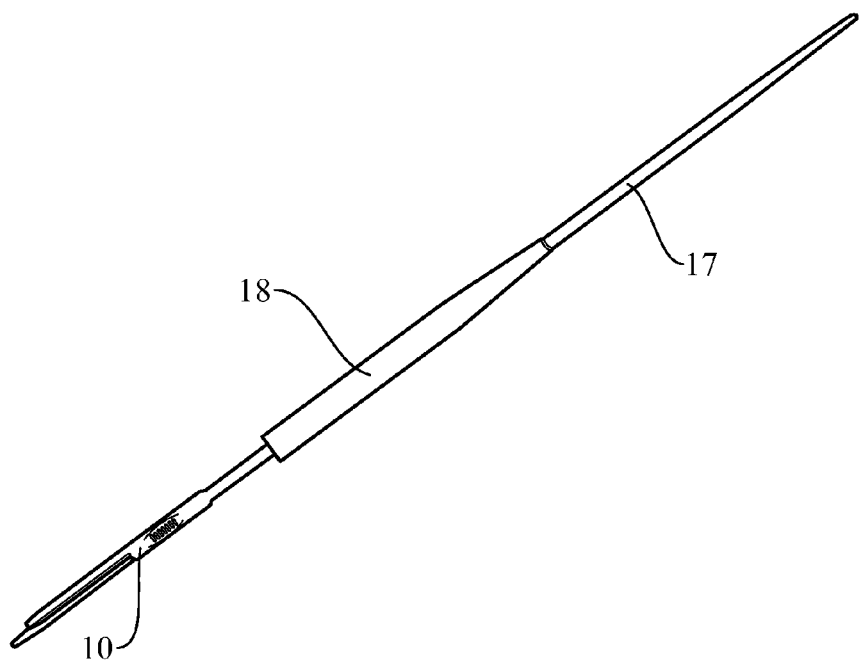
FIG. 7 is a side view of a flexible connection catheter tunneler assembly in one aspect of the invention.
Figure 8:
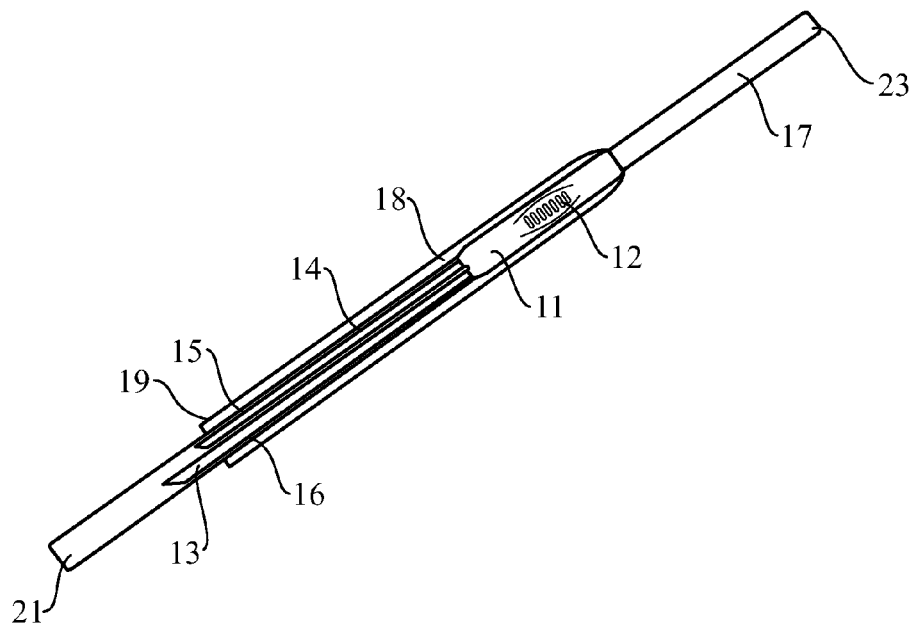
FIG. 8 is a sectional view of the flexible connection catheter tunneler of FIG. 7.

The inner surface of sheath 18 should also be configured to allow the tunneler shaft 17 to pass through the middle of the sheath (as shown in FIGS. 7 and 8). In one aspect of the invention, the inner surface of the sheath is illustrated in FIG. 5 so that the tunneler shaft 17 fits within the tapered tip 20 and is held in place by an interference or friction fit.

As well, as depicted in FIG. 5, the sheath 18 can contain an optional retention means. When used, the retention means helps retain the connector shaft(s) of the tunneler tip to the sheath. Any retention means known in the art serving this function can be used in the invention, including those depicted in FIG. 5. In FIG. 5, the retention means comprises retaining ring 19 that is configured to retain protrusions 15 on the connector shafts (as depicted in FIG. 8). The retaining ring 19 can have and size or shape that is integral with the protrusions 15. For example, the retention ring can generally be "raised" from the inner surface of the sheath from about 1 to about 3 mm.

Figure 6:
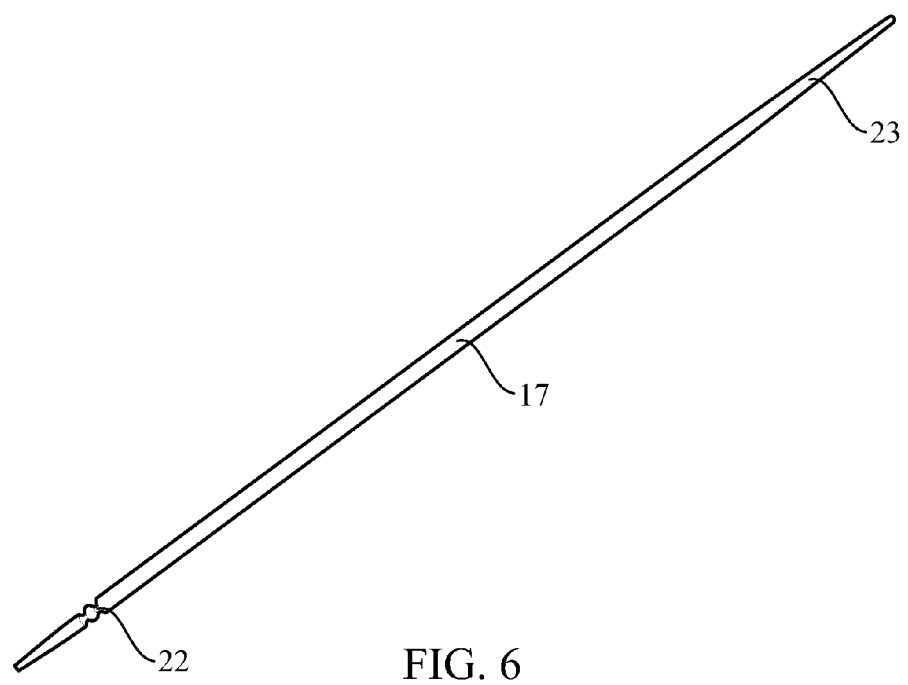
FIG. 6 is a side view of a tunneler segment in one aspect of the invention.

Besides the tip and the sheath, the tunneler system of the invention also contains a tunneler shaft. Any suitable shaft known in the art that creates the "tunnel" in the skin (as described above) can be use in the invention. In one aspect of the invention, the tunneler shaft 17 (or shaft 17) depicted in FIG. 6 is used in the invention. In FIG. 6, the illustrated segment of the shaft 17 contains a first end that is used in creating the tunnel during operation. Any mechanism known in the art that creates a tunnel can be used in the invention, including the tapered portion 23 depicted in FIG. 6. The taper of portion 23 can be any that provides the desired tunnel in the skin in an easy and quick manner.

At the other end, the shaft 17 contains a mechanism for connecting the shaft 17 to the tunneler tip 10. Any mechanism that operates in the manner can be used in shaft 17. In one aspect of the invention, this mechanism comprises a molded joint fastening grove 22. The fastening groove 22, as well as its operation, are described in detail below.

The tunneler shaft 17 can be made of any material that provide or enhance the function of the tunneler shaft described above. Examples of such materials include metals and their alloys, rigid plastics, and other ridged ceramic composts. In one aspect of the invention, the tunneler shaft comprises the metal alloy steel.

FIG. 7 illustrates the tunneling system of the invention, i.e., the tunneler shaft 17, sheath 18, and tunneler tip 10 as assembled together. As partially depicted in FIG. 7, the tunneler tip 10 is connected to tunneler shaft 17 by any suitable connection means. Any connection means known in the art can be used in the invention, including insert molding on the tip combined with the groove 22, or ferrules, screwing mechanisms, bonding and the like. In one aspect, the connection means comprises the fastening groove 22 which connects to a corresponding insert molding in the tunneler tip 10. The insert molding joint could be formed from a variety of methods as known in the art.

The tunneler sheath 18 is then placed over tunneler shaft 17 and tunneler tip 10 and held in place using any suitable restraining means between the sheath and the shaft. Examples of suitable restraining means between the sheath and the shaft include threads, snaps, and an interference or friction fit between the inner surface of the sheath and the outer surface of the tunneler tip. In one aspect of the invention, the restraining means comprises a slight friction fit. Examples of restraining means between the sheath and the tip include those described above.

The tunneling system of the invention can be used to create a tunnel in the skin for a medical device (i.e., catheter) as known in the art. In one aspect of the invention, the tunneling system is assembled used as illustrated in FIG. 8. As shown in FIG. 8, the tunneler tip 10 is inserted into the tip 21 of a catheter by grasping the grip surfaces 11 on the grip member 12. Then, the tapered end of the connection shaft (13) is inserted into the corresponding lumen of catheter tip 21. Next, the tapered end of the other connection shaft (14) is inserted into the corresponding lumen of catheter tip 21. In other words, the longer connection shaft can be inserted first in one side of a dual-lumen catheter and the shorter connection shaft can then be inserted in the other side of the dual lumen catheter. The flexibility and staggered lengths of the connection shafts 13 and 14 facilitate the continued insertion until the distal end of catheter tip 21 contacts grip member 12.

In this position, the protrusions 15 and 16 form smooth flared sections in the outer walls of catheter tip 21. The tunneler sheath 18 is then retracted down over tunneler shaft 17 towards and over catheter tip 21 until the tapered tip 20 of the sheath 20 contacts the grip member 12. At the same time, the retaining ring 19 slides over protrusions 15 and 16 to produce an internal and external lock on catheter tip 21.

After being connected in this manner, the tunneling system of the invention is then used to pull the catheter (or other medical device) through the tunnel and then placing the catheter in the desired location. The flexibility of the connector shafts 13 and 14 and the smooth surface of protrusions 15 and 16, combined with the retaining ring 19, allow the tunneler to be twisted or manipulated at various angles without damaging the catheter tip 21 and without becoming disconnected from the catheter.

Once through the tunnel, the user slides the sheath 18 over tunneler shaft 17, thereby releasing the internal and external lock produced by retaining ring 19 and protrusions 15 and 16. The tunneler tip 10 is then removed from the catheter tip 21 by gripping the grip surfaces 11 on the grip member 12 and pulling the tunneler tip 10 away from catheter tip 21.

In addition to any previously indicated variation, numerous other modification and alternative arrangements may be devised by those skilled in the art without departing from the spirit and scope of the invention and appended claims are intended to cover such modifications and arrangements. Thus, while the invention has been described above with particularity and detail in connection with what is presently deemed to be the most practical and preferred aspects of the invention, it will be apparent to those of ordinary skill in the art that numerous modifications, including but not limited to, form, function, manner of operations and use may be made without departing form the principles and concepts set forth herein.

What is claimed is:

1. A tunneler system, comprising:
   a multi-lumen catheter; and
   a tunneler removably retained to the catheter, comprising:
   a tip containing gripping means;
   a plurality of flexible connector shaft members having a first end extending from the tip and a second end that is closed, the plurality of connector shaft members having unequal lengths that are retained in the lumens of the catheter;
   a rigid tunneler shaft containing a first end with a tapered section that is closed and a second end proximate the tip and the tunneler shaft is removably connected to the tip at the second end; and
   a sheath that covers a portion of the tip and tunneler shaft that are connected, wherein the sheath is retained both on the tip and on the tunneler shaft using a retainer comprising a retainer ring.

2. The tunneler system of claim 1, wherein the retainer comprises an internal geometry of the sheath.

3. The tunneler system of claim 1, wherein the connector shaft member is retained in the catheter lumen by using a protrusion.

4. The tunneler system of claim 3, wherein the retainer complements the protrusion on the connector shaft member.

5. The tunneler system of claim 3, wherein each connector shaft member is retained in the catheter lumen by using a protrusion that is located near the second end of the connector shaft member.

6. The tunneler system of claim 3, wherein the protrusion is circular or oval in shape and raised above the surface of the connector shaft member about 2 mm.

7. The tunneler system of claim 1, wherein the difference in the lengths of the connector shaft member ranges up to about 20%.

8. The tunneler system of claim 7, wherein the difference in the lengths of the connector shaft member ranges from about 5% to about 20%.

9. The tunneler system of claim 1, wherein the retainer ring is raised above an inner surface of the sheath from about 1 to about 3 mm.

10. The medical apparatus of claim 1, wherein the retainer ring is raised above an inner surface of the sheath from about 1 to about 3 mm.

11. A medical apparatus containing a tunneler system, the tunneler system comprising:
   a multi-lumen catheter; and
   a tunneler removably retained to the catheter, comprising:
      a tip containing gripping means;
      a plurality of flexible connector shaft members having a first end extending from the tip and a second end that is closed, the plurality of connector shaft members having unequal lengths that are retained in the lumens of the catheter;
      a rigid tunneler shaft containing a first end with a tapered section that is closed and a second end proximate the tip and the tunneler shaft is removably connected to the tip at the second end; and
      a sheath that covers a portion of the tip and tunneler shaft that are connected, wherein the sheath is retained both on the tip and on the tunneler shaft using a retainer, wherein the connector shaft member is retained in the catheter lumen by using a protrusion and the retainer complements the protrusion on the connector shaft member.

12. The medical apparatus of claim 11, wherein the retainer comprises a retainer ring.

13. The medical apparatus of claim 11, wherein the retainer comprises an internal geometry of the sheath.

14. The medical apparatus of claim 11, wherein the difference in the lengths of the connector shaft member ranges up to about 20%.

15. The medical apparatus of claim 14, wherein the difference in the lengths of the connector shaft member ranges from about 5% to about 20%.

16. The medical apparatus of claim 11, wherein each connector shaft member is retained in the lumen by using a protrusion that is located near the second end of the connector shaft member.

17. The medical apparatus of claim 11, wherein the protrusion is circular or oval in shape and raised above the surface of the connector shaft member about 2 mm.

* * * * *